US008821882B2

(12) United States Patent
Nishikawa et al.

(10) Patent No.: US 8,821,882 B2
(45) Date of Patent: Sep. 2, 2014

(54) VACCINE PREPARATION FOR NEOSPORA CANINUM INFECTION

(75) Inventors: Yoshifumi Nishikawa, Hokkaido (JP); Naoaki Yokoyama, Hokkaido (JP); Naoya Kojima, Kanagawa (JP)

(73) Assignees: Obihiro University of Agriculture and Veterinary Medicine, Hokkaido (JP); Tokai University Educational System, Tokyo (JP)

( * ) Notice: Subject to any disclaimer, the term of this patent is extended or adjusted under 35 U.S.C. 154(b) by 439 days.

(21) Appl. No.: 13/119,629

(22) PCT Filed: Sep. 11, 2009

(86) PCT No.: PCT/JP2009/004525
§ 371 (c)(1),
(2), (4) Date: May 20, 2011

(87) PCT Pub. No.: WO2010/032408
PCT Pub. Date: Mar. 25, 2010

(65) Prior Publication Data
US 2011/0250265 A1    Oct. 13, 2011

(30) Foreign Application Priority Data

Sep. 17, 2008 (JP) ................................. 2008-237719

(51) Int. Cl.
*A61K 39/00* (2006.01)
*A61K 39/38* (2006.01)
(52) U.S. Cl.
USPC ...................................................... 424/184.1
(58) Field of Classification Search
None
See application file for complete search history.

(56) References Cited

U.S. PATENT DOCUMENTS 5,759,572 A    6/1998   Sugimoto et al.

FOREIGN PATENT DOCUMENTS

JP    H07-126185 A    5/1995
WO   WO 92/04887 A1   2/1992

OTHER PUBLICATIONS

Takagi et al. ( Cytokine vol. 40, pp. 241-250, 2007).*
Lally et al. ( Molecular and Biochemical Parasitology , vol. 87, pp. 239-243, 1997).*
Rudikoff et al (Proc Natl Acad Sci USA 1982 vol. 79 p. 1979).*
Burgess et al. (J of Cell Biology, 1990 vol. 111, pp. 2129-2138).*
Lazar et al (Molecular and Cellular Biology, 1988, vol. 8, pp. 1247-1252).*
International Preliminary Report on Patentability, corresponding with International Application PCT/JP2009/004525, (7) pages, Nov. 17, 2009.

Y. Noguchi et al., "Priming for in vitro and in vivo anti-human T lumphotropic virus type 1 cellular immunity by virus-related protein reconstituted into liposome", J. Immunol, May 15, 1991; 146(10):3599-603.
J.P. Dubey et al., "Epidemiology and Control of Neosporosis and Neospora caninum", Clinical Microbiology Reviews, vol. 20, No. 2, pp. 323-367, Apr. 2007.
Takeshi Mikami et al., "Saccharomyces cerevisiae", Abstract B1-05 (1993), pp. 43-44 [contains English Abstract].
Naoaki Yokoyama et al., "Genchu Kansensho ni Taisuru Oligomannose Tosa Hifuku Liposome Vaccine no Hyoka", The Japanese Society of Parasitology Taikai program Shorokushu, 2006, pp. 67, I-D-04 [with English translation].
Noritaka Kuboki et al., "Preliminary evaluation of oligomannose-coated liposome vaccines against lethal protozoan infections in mice", J. Protozool. Res., 2007, vol. 17, pp. 9-15.
N. Kuboki et al., "Adjuvant Effect of Oligomannose-Coated Liposome-Based Platform for Vaccine against African Trypanosomosis", J. Protozool. Res., 2008, vol. 18, pp. 1-10.
Y. Shimizu et al., "Intraperitoneal immunization with oligomannose-coated liposome-entrapped soluble-leishmanial antigen induces antigen-specific T-helper type immune response in BALB/c mice through uptake by peritoneal macrophages", Parasite Immunology, 2007, vol. 29, pp. 229-239.
Houshuang Zhang et al., "Apical membrane antigen 1 is a cross-reactive antigen between Neospora caninum and Toxoplasma gondii, and the anti-NcAMA1 antibody inhibits host cell invasion by both parasites", Molecular & Biochemical Parasitology, 2007, vol. 151, pp. 205-212.
Ramesh Vemulapalli et al., "Reduced cerebral infection of Neospora caninum in BALB/c mice vaccinated with recombinant Brucella abortus RB51 strains expressing N. caninum SRS2 and GRA7 proteins", Veterinary Parasitology, 2007, vol. 148, pp. 219-230.
Yoshifumi Nishikawa et al., "Neospora Kensengyu ni Okeru Ryuzan Kanren Bunshi no Kenshutsu", The Japanese Society of Veterinary Science Gakujutsu Shukai Koen Yoshishu, 2008, p. 186 CP4-3 [with English translation].
Yoshifumi Nishikawa et al., "Oligosaccharide Liposome o Mochiita Neospora Suichoku Kansen ni Taisuru Vaccine Kaihatsu", The Japanese Society of Veterinary Science Gakujutsu Shukai Koen Yoshishu, 2009, p. 228 CP2-1 [with English translation].
International Search Report corresponding with International Application No. PCT/JP2009?004525 dated Nov. 17, 2009.
H. Zhang et al., "Apical membrane antigen 1 is a cross-reactive antigen between Neospora caninum and Toxoplasma gondii, and the anti-NcAMA1 antibody inhibits host cell invasion by both parasites", Mol Biochem Parasitol, Feb. 2007; 151(2):205-12. Epub Nov. 30, 2006.
Y. Shimizu et al., "Intraperitoneal immunization with oligomannose-coated liposome-entrapped soluble leishmanial antigen induces antigen-specific T-helper type immune response in BALB/c mice through uptake by peritoneal macrophages", Parasite Immunol, May 2007; 29(5):229-39.

(Continued)

*Primary Examiner* — Gary B. Nickol
*Assistant Examiner* — Khatol Shahnan-Shah
(74) *Attorney, Agent, or Firm* — Pearne & Gordon LLP (57) ABSTRACT

A vaccine preparation characterized in that *Neospora caninum*-derived dense granule protein 7 or apical membrane antigen 1 or an immunologically active variant or derivative thereof is included in liposomes each having an oligosaccharide capable of binding to a carbohydrate recognition molecule on the surface of antigen-presenting cells on the surface of the liposome.

8 Claims, 6 Drawing Sheets

(56) References Cited

OTHER PUBLICATIONS

R. Vermulapalli et al., "Reduced cerebral infection of Neospora caninum in BALB/c mice vaccinated with recombinant Brucella abortus RB51 strains expressing N. caninum SRS2 and GRA7 proteins", Vet Parasitol, Sep. 30, 2007; 148(3-4):219-30. Epub Jul. 24, 2007.

S. Ramamoorthy et al., "Prevention of vertical transmission of Neospora caninum in C57BL/6 mice vaccinated with Brucella abortus strain RB51 expressing N. caninum protective antigens", Int. J. Parasitol, Nov. 2007; 37(13):1531-8. Epub May 13, 2007.

Y. Nishikawa et al., "Prevention of vertical transmission of Neospora caninum in BALB/c mice by recombinant vaccinia virus carrying NcSRS2 gene", Vaccine, Feb. 8, 2001; 19(13-14): 1710-6.

Y. Noguchi et al., "Priming for in vitro and in vivo anti-human T lumphotropic virus type 1 cellular immunity by virus-related protein reconstituted into liposome", J. Immunol, May 15, 1991; 146(10):3599-603.

International Search Report dated Nov. 6, 2009 from International Application No. PCT/JP2009/004525 (English).

* cited by examiner

Figure 1  NUMBER OF NEW-BORN MICE AND SURVIVAL RATE THEREOF DURING POSTNATAL 30 DAYS

| EXPERIMENTAL GROUP | EXPERIMENT | NUMBER OF PREGNANT MICE | NUMBER OF LIVE BIRTHS PER LITTER (STANDARD DEVIATION) | 30-DAY SURVIVAL NUMBER OF NEW-BORN MICE PER LITTER | 30-DAY SURVIVAL RATE OF NEW-BORN MICE |
|---|---|---|---|---|---|
| PBS | Trial 1 | 4 | 6.8 (2.6) | 2/3, 2/7, 0/8, 2/9 | 6/27 (22.2%) |
|  | Trial 2 | 5 | 7.2 (2.2) | 1/5, 0/8, 0/10, 4/8, 0/5 | 5/36 (13.4%) |
|  | Trial 3 | 4 | 7.8 (1.0) | 2/7, 2/7, 4/9, 7/8 | 15/31 (48.4%) |
|  | Total | 13 | 7.2 (1.9) |  | 26/94 (27.7%) |
| M3-GST | Trial 1 | 4 | 6.8 (1.7) | 0/7, 3/6, 1/9, 3/5 | 7/27 (25.9%) |
|  | Trial 2 | 5 | 6.4 (1.3) | 0/7, 3/5, 0/7, 1/8, 0/5 | 4/32 (12.5%) |
|  | Trial 3 | 2 | 4.5 (3.5) | 2/2, 5/7 | 7/9 (77.7%) |
|  | Total | 11 | 6.2 (1.9) |  | 18/98 (26.5%) |
| GRA7 | Trial 2 | 4 | 6.3 (2.6) | 2/8, 0/9, 1/4, 0/4 | 3/25 (12.0%) |
|  | Trial 3 | 3 | 7.3 (2.1) | 4/8, 3/5, 1/9 | 8/22 (36.4%) |
|  | Total | 7 | 6.7 (2.3) |  | 11/47 (23.4%) |
| M3-GRA7 | Trial 1 | 4 | 6.5 (1.3) | 5/7, 8/8, 3/6, 3/5 | 19/26 (73.1%) |
|  | Trial 2 | 5 | 5.0 (2.6) | 2/4, 0/2, 5/6, 7/9, 2/4 | 16/25 (64.0%) |
|  | Trial 3 | 4 | 7.0 (1.2) | 2/8, 6/6, 8/8, 6/6 | 22/28 (78.6%) |
|  | Total | 13 | 6.1 (2.0) |  | **57/79 (72.2%) \*\*** |
| AMA1 | Trial 2 | 4 | 6.3 (2.5) | 2/9, 0/7, 0/6, 0/3 | 2/25 (8.0%) |
|  | Trial 3 | 2 | 7.5 (0.7) | 3/7, 3/8 | 6/15 (40.0%) |
|  | Total | 6 | 6.7 (2.1) |  | 8/40 (20.0%) |
| M3-AMA1 | Trial 1 | 4 | 6.0 (2.2) | 4/6, 6/8, 1/3, 4/7 | 15/24 (62.5%) |
|  | Trial 2 | 5 | 5.2 (1.6) | 2/7, 3/4, 1/3, 3/6, 6/6 | 15/26 (57.7%) |
|  | Trial 3 | 2 | 5.0 (0) | 5/5, 5/5 | 10/10 (100%) |
|  | Total | 9 | 5.1 (2.0) |  | **40/60 (66.7%) \*\*** |
| M3-SRS2 | Trial 1 | 4 | 5.5 (0.6) | 1/5, 1/6, 0/5, 3/6 | 5/22 (22.7%) |
|  | Total | 4 | 5.5 (0.6) |  | 5/22 (22.7%) |

\*\* $P < 0.01$

Figure 2    SURVIVAL CURVE OF NEW-BORN MICE

Figure 3  NEOSPORA CANINUM INFECTION RATE OF MOTHER MICE

| EXPERIMENTAL GROUP | EXPERIMENT | RATE OF NEOSPORA CANINUM INFECTION |
|---|---|---|
| PBS | EXPERIMENT 1 | 4/4 (100%) |
| | EXPERIMENT 2 | 5/5 (100%) |
| | TOTAL | 9/9 (100%) |
| M3-GST | EXPERIMENT 1 | 4/4 (100%) |
| | EXPERIMENT 2 | 5/5 (100%) |
| | TOTAL | 9/9 (100%) |
| GRA7 | EXPERIMENT 2 | 4/4 (100%) |
| M3-GRA7 | EXPERIMENT 1 | 1/4 (25%) |
| | EXPERIMENT 2 | 2/5 (40%) |
| | TOTAL | 3/9 (33.3%) * |
| AMA1 | EXPERIMENT 2 | 4/4 (100%) |
| M3-AMA1 | EXPERIMENT 1 | 2/4 (50%) |
| | EXPERIMENT 2 | 2/5 (40%) |
| | TOTAL | 4/9 (44.4%) * |
| M3-SRS2 | EXPERIMENT 1 | 4/4 (100%) |

* $P < 0.01$

Figure 4 PRODUCTION OF ANTIBODY TO IMMUNOGEN

Figure 5 PRODUCTION OF ANTIBODY TO *NEOSPORA CANINUM*

Figure 6 CYTOKINE PRODUCTION

VACCINE PREPARATION FOR NEOSPORA CANINUM INFECTION

CROSS-REFERENCE TO RELATED APPLICATIONS

This is the U.S. National Phase of International Application PCT/JP2009/004525, filed Sep. 11, 2009, and claims priority benefit under 35 U.S.C. §119 based on Japanese Application No. 2008-237719, filed Sep. 17, 2008, the entire disclosures, including Sequence Listings, of which applications are hereby incorporated herein by reference.

TECHNICAL FIELD

The present invention relates to a vaccine preparation for *Neospora caninum* infection and more specifically to a vaccine preparation in which a soluble protein derived from *Neospora caninum* is included in liposomes each having an oligosaccharide capable of binding to a carbohydrate recognition molecule on the surface of antigen-presenting cells on the surface of the liposome.

BACKGROUND ART

*Neospora caninum* is an intracellular parasitic protozoon using an animal belonging to the canine family as a final host and cattle, sheep, a goat, deer, or the like as an intermediate host. The *Neospora* is transmitted by horizontal infection from oocyst discharged in the feces of a final host or by vertical infection in an intermediate host and, particularly in cattle, causes miscarriage, stillbirth, or abnormal labor mainly characterized by neurological symptoms in calf at a high rate. *Neospora caninum* infection is estimated to account for about 40% of bovine miscarriage cases in reports from Western countries. The vertical infection with *Neospora caninum* has been established over repeated generations, which is cited as a biggest factor in the spread of infection with the protozoon. In fact, cases of infection with *Neospora caninum* have been reported all over the world, and its occurrence is also serious in Japan. Bovine dams infected with *Neospora caninum* cannot often be milked, leading to the wastage of calves and the milking amount and the like; thus, its occurrence causes remarkably large economic loss in the livestock industry. There is also an estimation that global damage due to *Neospora caninum* infection annually aggregates about billions of US dollars.

The following needs to be considered for a vaccine for preventing the *Neospora caninum* infection. Because *Neospora caninum* is an intracellular parasitic protozoon, cellular immunity is important for protective immunity thereagainst. Particularly, the function of interferon gamma and CD4-positive T cells is important. The effect of antibody on *Neospora caninum* is a controversial subject; however, the antibody is believed to react to *Neospora caninum* present outside the cells to prevent the spread thereof in the body.

Infection during pregnancy causes miscarriage or vertical infection due to the characteristic immune response of the mother's body. That is, when *Neospora caninum* infection occurs during early pregnancy, miscarriage is induced by the immune reaction of the mother's body. When *Neospora caninum* infection occurs during mid-pregnancy during which the mother's body is immunosuppressed, vertical infection to the fetus is established, and an individual congenitally infected with *Neospora caninum* is born.

Some vaccines against *Neospora caninum* using inactivated and live forms of the protozoon have previously been attempted to be developed on bovine neosporosis. The use of the inactivated *Neospora caninum* and POLYGEN as an adjuvant could not prevent the infection of fetuses therewith (Non Patent Literature 1). The use of the inactivated *Neospora caninum* and HAVLOGEN as an adjuvant is reported to have a prophylactic effect of 5.2% to 54% in New Zealand and of 46% in Costa Rica (Non Patent Literature 1). Vaccination with the live vaccine is also reported to have the effect of reducing stillbirth. However, the effect of these vaccines on naturally-infected cattle has not yet been demonstrated.

In addition to the inactivated and live vaccines, recombinant vaccines targeting proteins derived from *Neospora caninum* have been attempted to be prepared. Experiments using a mouse model resulted in the vertical infection thereof with the protozoon being suppressed by recombinant vaccines using *Neospora caninum*-derived proteins: MIC1, MIC3, GRA2, GRA6, SAG1 and SRS2 (Non Patent Literatures 2 and 3).

However, vectors derived from a microorganism and a virus were used for the preparation of the above recombinant vaccines; thus, the pathogenicity of these vectors is a problem in vaccinating an animal therewith. Accordingly, to prepare a recombinant vaccine, it represents a challenge to develop a vector and an adjuvant high in safety and excellent in the ability to induce cellular immunity.

Liposomes coated with a macromolecular polysaccharide such as mannan developed as an adjuvant for vaccines and immunotherapy are reported to have a strong ability to induce cellular immunity (Patent Literature 1 and Non Patent Literature 4). However, mannan is a mixture of polymannoses with heterogeneous molecular weights and also has strong toxicity to a living body (Non Patent Literature 5); thus, it is not suitable for a pharmaceutical product.

Meanwhile, Mizuochi et al. reports that an antigen is included in liposomes whose surface has an oligosaccharide comprising 2 to 11 sugar residues and binding to a lectin derived from antigen-presenting cells to remove the toxicity and antigenicity of the sugar and enhance its effect as a vaccine (Patent Literature 2). This document also discloses that cellular immunity against the antigen included in the liposomes each having the oligosaccharide on the surface can be efficiently induced. The liposome having the oligosaccharide on the surface is thought to be phagocytized by antigen-presenting cells via mannose receptors, resulting in the presentation of the antigen through an MHC class I or II molecule for the activation of antigen-specific T cells and the induction of Th1-derived cytokines.

Shimizu et al. report that when a *Leishmania major*-derived soluble antigen is included in liposomes each having an oligosaccharide on the surface and mice are immunized with these liposomes, Th1-type immunity against *Leishmania major* is significantly induced to control the infection of the mice with the protozoon (Non Patent Literature 6).

CITATION LIST

Patent Literature

Patent Literature 1: International Publication No. WO 92/04887
Patent Literature 2: Japanese Patent No. 2828391

Non Patent Literature

Non Patent Literature 1: Dubey et al., Clinical Microbiology Reviews 2007 20: 323-367

Non Patent Literature 2: Ramamoorthy et al., Int. J. Parasitol. 2007, 37: 1531-1538
Non Patent Literature 3: Nishikawa et al., Vaccine 2001, 19: 1710-1716
Non Patent Literature 4: Noguchi et al., J. Immunol. 1991, 146: 3599-3603
Non Patent Literature 5: Mikami et al., 15th Carbohydrate Symposium, Abstract 1993, 43-44
Non Patent Literature 6: Shimizu et al., Parasite Immunol. 2007, 29: 229-239

SUMMARY OF INVENTION

Technical Problem

An object of the present invention is to provide a safe vaccine preparation capable of inducing an effective immune response to *Neospora caninum* infection and to achieve the enhancement of a prophylactic effect against the *Neospora caninum* infection.

Solution to Problem

As a result of intensive studies for solving the above-described problems, the present inventors have found that a *Neospora caninum*-derived soluble protein is included in liposomes each having an oligosaccharide capable of binding to a carbohydrate recognition molecule on the surface of antigen-presenting cells on the surface of the liposome to improve the balance between Th1-type and Th2-type responses to *Neospora caninum* to remarkably enhance the vaccine effect thereof.

The present invention is based on such findings and relates to a liposome preparation in which *Neospora caninum*-derived dense granule protein 7 or apical membrane antigen 1 or an immunologically active variant or derivative thereof is included in liposomes each having an oligosaccharide capable of binding to a carbohydrate recognition molecule on the surface of antigen-presenting cells on the surface of the liposome.

Examples of the carbohydrate recognition molecule on the surface of antigen-presenting cells can include a mannose receptor.

In one embodiment, the dense granule protein 7 or an immunologically active variant or derivative thereof is, for example:

(a) a protein comprising the amino acid sequence shown in SEQ ID NO: 1 or (b) a protein comprising an amino acid sequence in which one or several amino acids are deleted, substituted, or added in the amino acid sequence shown in SEQ ID NO: 1 and capable of inducing an immune response to *Neospora caninum*.

The apical membrane antigen 1 or an immunologically active variant or derivative thereof is, for example,:

(c) a protein comprising the amino acid sequence shown in SEQ ID NO: 2 or (d) a protein comprising an amino acid sequence in which one or several amino acids are deleted, substituted, or added in the amino acid sequence shown in SEQ ID NO: 2 and capable of inducing an immune response to *Neospora caninum*.

The oligosaccharide used consists preferably of 2 to 11 sugar residues, more preferably of 3 to 7 sugar residues, most preferably of 3 to 5 sugar residues.

Preferred oligosaccharides can include a carbohydrate comprising 2 or more mannose.

The liposome preparation of the present invention can be used as a vaccine preparation for *Neospora caninum* infection. It is desirable that the vaccine preparation be formulated together with a pharmaceutically acceptable carrier and administered, for example, subcutaneously, intradermally, intravenously, orally, or nasally.

Advantageous Effects of Invention

The vaccine preparation provided in the present invention has a high prophylactic effect while having a reduced risk of side effects. Use of the vaccine preparation according to the present invention can prevent the vertical infection of fetuses with *Neospora caninum* as well as the infection of vaccinated individuals therewith.

The present specification encompasses the content of the specification of Japanese Patent Application No. 2008-237719 on which the priority of the present application is based.

DESCRIPTION OF EMBODIMENTS

The present invention relates to a liposome preparation in which *Neospora caninum*-derived dense granule protein 7 or apical membrane antigen 1 or an immunologically active variant or derivative thereof is included in liposomes each having an oligosaccharide capable of binding to a carbohydrate recognition molecule on the surface of antigen-presenting cells on the surface of the liposome, and a vaccine preparation for *Neospora caninum* infection comprising the liposome preparation.

The present invention will be described below in detail.

1. *Neospora caninum*

A protozoon is a eukaryotic unicellular microorganism and is an animal unicellular organism having motor and predatory abilities. For differentiation from a unicellular parasite, a parasitic and particularly pathogenic organism is also often called a protozoon. Protozoa include a highly host-specific type capable of being parasitic only in humans (*Plasmodium* spp., *Isospora* spp., or the like) and a type parasitic in a plurality of animal species and causing zoonotic infection (*Entamoeba histolytica, Cryptosporidium*, or the like). They vary in pathogenicity from those inducing lethal infections or serious symptoms to those inducing no symptom and having non-pathogenicity. Protozoa parasitic in the digestive tract orally invade a human body via drinking water or food. The infection form varies depending on the type of the protozoon; examples thereof include an encysted cyst, an oocyst, and a spore. *Entamoeba histolytica, Giardia lamblia*, and the like form cysts, *Coccidia* form oocysts, and *Microsporidia* form spores. Most protozoa parasitic in the blood and tissue proliferate in the intestinal tract of certain blood sucking insects and ixodids, and infect a human body using these as mediators.

*Neospora caninum* is an intracellular parasitic protozoon utilizing an animal belonging to the canine family as a final host and cattle, sheep, a goat, deer, or the like as an intermediate host. *Neospora caninum* is transmitted by horizontal infection from oocyst discharged in the feces of a final host or by vertical infection via an intermediate host. *Neospora caninum* is parasitic in epithelial cells, mononuclear cells in the cerebrospinal fluid, and nerve cells in a host, and, particularly in cattle, causes miscarriage, stillbirth, or abnormal labor mainly characterized by neurological symptoms in calf at a high rate. It causes polymyositis or ascending paralysis in dogs. A sulfonamide, erythromycin, doxycycline, or clindamycin is used for the treatment thereof; however, an effective prophylaxis has not been established.

For *Neospora caninum* infection, the development of a vaccine is under way which uses *Neospora caninum* itself or a soluble protein derived therefrom: MIC1, MICS, GRA2, GRA6, SAG1, SRS2, or the like; however, a sufficient effect has not been obtained.

2. Dense Granule Protein 7 (GRA7) and Apical Membrane Antigen 1 (AMA1)

According to the present invention, dense granule protein 7 (GRA7) and apical membrane antigen 1 (AMA1) are used as *Neospora caninum*-derived soluble proteins for inducing immune response.

GRA7 is an antigen molecule present in an organelle, the dense granule, in *Neospora caninum*, and sometimes called NcGRA7 or NcDG1 in addition to GRA7. The amino acid sequence of *Neospora caninum* GRA7 and the gene sequence encoding the same are already known and deposited in the public database GenBank under Accession Number U82229.

AMA1 is an antigen molecule present in the apical domain in *Neospora caninum* and also called NcAMA1 in addition thereto. The amino acid sequence of *Neospora caninum* AMA1 and the gene sequence encoding the same are already known and deposited in the public database GenBank under Accession Number AB265823.

GRA7 or AMA1 used for the present invention may also be a region in which a hydrophobic region or a signal sequence is removed in the constituting amino acid sequence; when an amino sequence from the initiation codon to the stop codon is used, the length of the amino acid sequence is not limited.

The amino acid sequence of *Neospora caninum* GRA7 is shown in SEQ ID NO: 1 and the amino acid sequence of *Neospora caninum* AMA1 is shown in SEQ ID NO: 2. However, the amino acid sequence of GRA7 or AMA1 is not limited to the amino acid sequence shown in SEQ ID NO: 1 or 2, and may be a sequence in which one or several amino acids are deleted, substituted, or added in the amino acid sequence shown in SEQ ID NO: 1 or 2, provided that it has a desired immunogenicity. The term "several amino acids" preferably means 2 to 7, more preferably 2 to 5, most preferably 2 to 3 amino acids. The amino acid substitution is preferably conservative substitution between analogous amino acid residues; examples thereof can include substitution between amino acids such as glycine (Gly) and proline (Pro), glycine and alanine (Ala) or valine (Val), leucine (Leu) and isoleucine (Ile), glutamic acid (Glu) and glutamine (Gln), aspartic acid (Asp) and asparagine (Asn), cysteine (Cys) and threonine (Thr), threonine and serine (Ser) or alanine, and lysine (Lys) and arginine (Arg).

Alternatively, the amino acid sequence of GRA7 or AMA1 may be a protein having a homology of at least 70% or more, preferably 80% or more, more preferably 90% or more, still more preferably 95% or more, particularly preferably 97%, 98% or 99% or more with the amino acid sequence shown in SEQ ID NO: 1 or 2 when calculated using BLAST or the like (for example, when the default in Blast, that is, the initial condition parameters, are used), provided that it has a desired immunogenicity.

Thus, the "immunologically active variant or derivative" according to the present invention includes an slightly altered or modified GRA7 or AMA1 protein, a fused protein between GRA7 or AMA1 and another peptide, or the like provided that it can induce immune response activity against *Neospora caninum* in a living body to which it was administered (for example, antigenicity, receptor binding, formation of a complex by the binding of the peptide by an MHC class I or class II molecule, and the like).

3. Preparation of GRA7 and AMA1

3.1 Preparation from *Neospora caninum*: The preparation of GRA7 and AMA1 used for the present invention can be by a method which involves performing purification by general column work from a natural product containing a *Neospora caninum*-derived soluble protein, e.g., *Neospora caninum*; the step of subjecting the resultant *Neospora caninum*-derived soluble protein to partial decomposition for carbohydrate removal, modification, or the like may be further added as needed.

3.2 Recombinant Production

Using a microorganism such as *Escherichia coli*, animal cells, or a plant, all or part of the GRA7 or AMA1 gene of *Neospora caninum* may be introduced and expressed to prepare a recombinant protein.

A vector for preparing the recombinant protein can be obtained by linking (inserting) a gene encoding GRA7 or AMA1 into a known vector. The vector is not particularly limited provided that it can be replicated in a host; examples thereof include plasmid DNA and phage DNA. Examples of the plasmid DNA include *Escherichia coli*-derived plasmids (e.g., pBR322, pBR325, pUC18, pUC119, pTrcHis, and pBlueBacHis), *Bacillus subtilis*-derived plasmids (e.g., pUB110 and pTP5), yeast-derived plasmids (e.g., YEp13, YEp24, YCp50, and pYE52), and plasmids for plant cell hosts (pBI221, pBI121). Examples of the phage DNA include λ phage. In addition, an animal virus such as retrovirus or vaccinia virus and an insect virus vector such as baculovirus may be used.

To insert the gene of the present invention into a vector, for example, a method is adopted which involves first cutting purified DNA using a suitable restriction enzyme and inserting the resultant into the restriction enzyme site or multicloning site of a suitable vector DNA for linkage to the vector. The gene of the present invention needs to be introduced after operably linking the gene to a promoter depending on a host. Here, "operably" refers to that through the promoter activity, the gene of the present invention located downstream of the promoter is suitably expressed in a host to exert the function thereof. The type of the promoter used is properly determined depending on the host cell; however, the details will be described in the next section.

In addition to the promoter and the gene of the present invention, the vector of the present invention may contain, if desired, a cis element such as an enhancer, a splicing signal, a poly(A) addition signal, a transformation marker gene (for example, dehydrofolate reductase gene, ampicillin resistance gene, neomycin resistance gene, kanamycin resistance gene, hygromycin resistance gene, bialaphos resistance gene, carboxin resistance gene, and phleomycin resistance gene), a ribosome-binding sequence (SD sequence), and the like.

A transformant for producing a recombinant protein can be obtained by introducing the above vector into a suitable host. The host is not particularly limited provided that it can express the GRA7 or AMA1 gene of the present invention. Examples thereof include bacteria belonging to the genus *Escherichia* such as *Escherichia coli*, the genus *Bacillus* such as *Bacillus subtilis*, the genus *Pseudomonas* such as *Pseudomonas putida* and the genus *Rhizobium* such as *Rhizobium meliloti*; yeasts such as *Saccharomyces cerevisiae* and *Schizosaccharomyces pombe*; *Aspergillus oryzae*; animal cells such as COS cells and CHO cells; and insect cells such as Sf9 and Sf21.

When a bacterium such as *Escherichia coli* is used as a host, it is preferable that the vector of the present invention is capable of autonomous replication in the bacterium while comprising a promoter, a ribosome-binding sequence, the gene of the present invention, and a transcription termination sequence. The vector may also contain a gene controlling the promoter. Examples of the *Escherichia coli* include *Escherichia coli* HMS174 (DE3), K12 and DH1; examples of the *Bacillus subtilis* include *Bacillus subtilis* MI 114 and 207-21. The promoter therefor is not particularly limited provided that it enables expression in the above host such as *Escherichia coli*; examples thereof include promoters derived from *Escherichia coli* and phage, such as a trp promoter, a lac promoter, a PL promoter, and a PR promoter. Artificially designed/altered promoters such as a tac promoter may also be used. A method for introducing the vector into bacteria is not particularly limited; examples thereof can include a method using calcium ion [Cohen, S, N. et al.: Proc. Natl. Acad. Sci., USA, 69: 2110-2114 (1972)] and an electroporation method.

When yeast is used as a host, for example, *Saccharomyces cerevisiae*, *Schizosaccharomyces pombe*, or *Pichia pastoris* is used. The promoter therefor is not particularly limited provided that it enables expression in yeast; examples thereof can include a gal1 promoter, gal10 promoter, a heat shock protein promoter, an MFα1 promoter, a PH05 promoter, a PGK promoter, a GAP promoter, a ADH promoter, and a AOX1 promoter. A method for introducing the vector into the yeast is not particularly limited; examples thereof can include an electroporation method [Becker, D. M. et al.: Methods. Enzymol., 194: 182-187 (1990)], a spheroplast method [Hinnen, A. et al.: Proc. Natl. Acad. Sci., USA, 75: 1929-1933 (1978)], and a lithium acetate method [Itoh, H.: J. Bacteriol., 153: 163-168 (1983)].

When *Aspergillus oryzae* is used as a host, examples of the promoter include a GlaA promoter (Hata et al. Curr. Genet., Vol 22, 85-91, 1992), an AmyB promoter (Tuchiya et al. Biosci. Biotechnol. Biochem., Vol 46, 1849-1853, 1992), and a No. 8 promoter (Ozeki et al. Biosci. Biotech. Biochem., Vol 60, 383-389, 1996). A method for introducing the vector into *Aspergillus oryzae* is not particularly limited; for example, an electroporation method or a calcium ion method can be used.

The GRA7 or AMA1 protein can be obtained by culturing the above transformant (host cells) in a suitable medium and collecting a desired protein from the culture. The transformant may be cultured according to an ordinary method. For example, a transformant using a microorganism such as *Escherichia coli* or yeast as a host may be cultured in a natural or synthetic medium containing carbon and nitrogen sources and inorganic salts capable of being assimilated by the microorganism and enabling the transformant to be efficiently cultured. When a plant cell is used as a host, the transformant may be cultured in a medium for plant cells, to which vitamins such as thiamine and pyridoxine are added.

The carbon source used is a carbohydrate such as glucose, fructose, sucrose or starch, an organic acid such as acetic acid or propionic acid, or an alcohol such as ethanol or propanol. The nitrogen source used is ammonia, an inorganic or organic acid ammonium salt such as ammonium chloride, ammonium sulfate, ammonium acetate or ammonium phosphate, or any of other nitrogen-containing compounds, or peptone, meat extract corn steep liquor, or the like. The inorganic substance used is potassium primary phosphate, potassium secondary phosphate, magnesium phosphate, magnesium sulfate, sodium chloride, ferrous sulfate, manganese sulfate, copper sulfate, calcium carbonate, or the like.

In the medium, an antibiotic such as ampicillin or tetracycline may be added to the medium, if necessary. When a microorganism transformed with a vector using an inducible promoter as a promoter is cultured, an inducer may be added to the medium, if necessary. For example, isopropyl-β-D-thiogalactopyranoside (IPTG) or the like may be added to the medium when a microorganism transformed with a vector using a Lac promoter is cultured, and indoleacrylic acid (IAA) or the like, when a microorganism transformed with a vector using a trp promoter is cultured.

The culture is typically carried out at about 30 to 37° C. for the order of 6 hours to 3 days under aerobic conditions such as shake culture and aerated and agitated culture. The pH is kept at a value of the order of 7.0 to 7.5 during the period of culture. The pH is adjusted using an inorganic or organic acid, an alkali solution, or the like. After culture, when the protein of the present invention is produced in bacterial bodies or in cells, the bacterial bodies or the cells are crushed to extract the protein. When the protein of the present invention is produced outside the bacterial bodies or outside the cells, the culture solution is directly used or subjected to removal of the bacterial bodies or the cells by centrifugation or the like. Thereafter, the protein of the present invention can be isolated and purified from the above culture using a general biochemical method used for the isolation and purification of protein, such as ammonium sulphate precipitation, SDS-PAGE, gel chromatography, ion exchange chromatography, hydrophobic chromatography or affinity chromatography, alone or in a proper combination thereof.

In addition to the above method, a peptide fragment containing a partial sequence or T-cell epitope of GRA7 or AMA1 may be prepared by protein engineering or by peptide synthesis.

4. Liposome 4.1 Lipid Constituting Liposome

The lipid constituting the liposome used for the present invention may be a common lipid known to constitute a liposome. Examples thereof include lipids derived from egg yolk, soybean, or other natural products from animals and plants, lipids whose unsaturation degree is reduced by hydrogenation thereof, or synthesized lipids; these lipids may be used alone or in a combination of a plurality thereof.

As will hereinafter be described, an amino group on a phospholipid is reacted with an aldehyde group of an oligosaccharide in the introduction of the oligosaccharide. Thus, the phospholipids used for the present invention are preferably those with amino groups, which may be used alone or in a combination of two or more thereof. The two fatty acid residues in the 1- and 2-positions of each phospholipid may be arbitrarily selected and may be those derived from natural products or synthetic products; fatty acid residues each having 4 to 30 carbons may be used which are derived from mixed fatty acids, saturated fatty acids, unsaturated fatty acids, polymerizable fatty acids, or the like. Preferred saturated fatty acids include those each having 12 to 24 carbons; examples thereof include lauric acid, myristic acid, palmitic acid, and stearic acid. Preferred unsaturated fatty acids include those each having 14 to 22 carbons and 1 to 6 unsaturated bonds; examples thereof include oleic acid, linoleic acid, and arachidonic acid. Of these phospholipids having amino groups, those derived from natural products are preferably phospholipids derived from egg yolk or soybean. Suitable examples thereof include phosphatidylethanolamine, phosphatidylserine or phosphatidylthreonine, dipalmitoylphosphatidylethanolamine, and dipalmitoyl phosphatidylcholine.

The membrane constituent (membrane-forming component) of the liposome may use a different compound capable of forming a liposome in addition to the phospholipid having an amino group, provided that a carbohydrate can be introduced thereinto. For example, compounds each conventionally used as a membrane constituent of a liposome may be used such as soybean lecithin, egg-yolk lecithin, phosphatidylglycerol, other phospholipids, cholesterols, fatty acids, and fatty acid salts.

Specific examples thereof include sterols such as cholesterol (Chol), 3β-[N-(dimethylaminoethane)carbamoyl]cholesterol (DC-Chol), and N-(trimethylammonioethyl)carbamoylcholesterol (TC-Chol); phosphatidylethanolamines such as dipalmitoylphosphatidylethanolamine (DPPE) and distearoylphosphatidylethanolamine (DSPE); phosphatidylcholines such as dipalmitoylphosphatidylcholine (DPPC) and distearoylphosphatidylcholine (DSPC); phosphatidylserines such as dipalmitoylphosphatidylserine (DPPS) and distearoylphosphatidylserine (DSPS); and phosphatidic acids such as dipalmitoylphosphatidic acid (DPPA) and distearoylphosphatidic acid (DSPA).

The liposome may be a multilamellar liposome or a unilamellar liposome. The particle diameter of the liposome used for the present invention is not particularly limited; however, it is 0.1 to 3 μm, preferably 0.2 to 2.5 μm. This is because a liposome particle diameter of more than the upper limit causes the liposomes to gelate, which does not enable the use thereof in a vaccine. The particle diameter of the liposome can be adjusted according to an ordinary method depending on the dosage form used, for example, by filtration using a filter having a desired pore size.

4.2 Oligosaccharide on Surface of Liposome

The liposome used for the present invention has an oligosaccharide capable of binding to a carbohydrate recognition molecule on the surface of antigen-presenting cells on the surface of the liposome. Here, the "antigen-presenting cells" mean macrophages, dendritic cells, or the like. On the surface of antigen-presenting cells are present an Fc receptor and a complement receptor, a scavenger receptor, a mannose receptor, a lipopolysaccharide (LPS) receptor, CD11b/CD18 (CR3) also as a complement receptor, a Toll-like receptor, and the like, which directly or indirectly play important roles in the phagocytosis of bacteria and the like via a carbohydrate and in the uptake of a glycoprotein in an exogenous foreign material and the presentation of its antigen. The "carbohydrate recognition molecule on the surface of antigen-presenting cells" according to the present invention means any molecule having carbohydrate-binding lectin-like properties present on the surface of antigen-presenting cells as described above; preferred examples thereof can include a mannose receptor.

The oligosaccharide on the surface of the liposome is not particularly limited provided that it can bind to the above-described carbohydrate recognition molecule on the surface of antigen-presenting cells; examples of sugar residues constituting the oligosaccharide include D-mannose (D-Man), L-fucose (L-Fuc), D-acetylglucosamine (D-GlcNAc), D-glucose (D-Glc), D-galactose (D-Gal), D-acetylgalactosamine (D-GalNAc), and D-rhamnose (D-Rha). The oligosaccharide is preferably a high-mannose type oligosaccharide consisting of sugar residues including D-mannose; among others, preferred are an oligosaccharide consisting of D-mannose and an oligosaccharide consisting of D-mannose and D-acetylglucosamine, and particularly, an oligosaccharide consisting only of D-mannose is most preferable. Examples of the oligosaccharide consisting of D-mannose can include mannobiose (Man2), mannotriose (Man3), mannotetraose (Man4), mannopentaose (Man5), mannohexaose (Man6), and mannoheptaose (Man7).

The binding between the sugar residues constituting the oligosaccharide is not particularly limited; examples thereof can include α1→2 binding, α1→3 binding, α1→4 binding, α1→6 binding, and β1→4 binging. The sugar residues may bind one after another in a straight chain form or may bind so as to form a branched structure.

The number of the sugar residues constituting the oligosaccharide is preferably 2 to 11, particularly 3 to 11, and most preferably about 3 to 5.

The amount of the oligosaccharide based on the liposome varies depending on the type of the oligosaccharide, the type of a *Neospora caninum*-derived soluble protein to be included, the combinational structure of the liposome, and the like; however, it is typically 0.5 μg to 500 μg based on 1 mg of the lipid constituting the liposome.

The oligosaccharide can be introduced into the liposomes using an artificial glycolipid prepared by causing the oligosaccharide to bind to a lipid. The artificial glycolipid can be prepared by causing the oligosaccharide to bind to the lipid by reacting an aldehyde group of the oligosaccharide with a phospholipid having an amino group to form a Schiff base and then reducing the Schiff base according to an ordinary method, preferably by chemical reduction, for example, by reduction using NaBH$_3$CN (Tsugio Mizuochi, Toshitsu Kogaku (in Japanese), 224-232, 1992). Subsequently, using the artificial glycolipid, the oligosaccharide is introduced into the liposomes. When the artificial glycolipid is water-soluble and not sufficiently dissolved in an organic solvent (for example, when the artificial glycolipid uses a bound substance of the above-described RN and DPPE (RN-DPPE)), an aqueous solution thereof (of RN-DPPE) is prepared and mixed with the liposomes, which is then incubated, for example, at 4° C. to 80° C. (preferably, a temperature at which an inclusion is not denatured), room temperature or a phase transition temperature for 0.5 to 120 hours, for example, for about 24 hours. When the artificial glycolipid is soluble in an organic solvent, the artificial glycolipid may be dissolved together with a lipid for constituting a liposome in the organic solvent during a liposome production process to form liposomes according to an ordinary method. In this respect, the binding of the oligosaccharide to the surface of the liposome may be examined by whether a liposome aggregation reaction occurs by the addition of a carbohydrate recognition molecule or a portion thereof present on the surface of the antigen-presenting cells.

4.3 Making Liposome Preparation

The liposome preparation of the present invention is produced by including the above-described GRA7 or AMA1 protein in the liposomes. The amount of the GRA7 or AMA1 protein included is not particularly limited and can be properly adjusted depending on the administration route thereof;

however, it is preferably typically 0.1 µg to 500 µg based on 1 mg of the lipid used in the liposome.

5. Vaccine Preparation

The vaccine preparation of the present invention is prepared such that it can be administered in the form of a solution or a suspension by properly adding a pharmaceutically acceptable carrier to the liposome preparation of the present invention. A pharmaceutically acceptable diluent compatible with the active ingredient is often mixed in the vaccine preparation of the present invention. Suitable diluents include, for example, water, saline, dextrose, glycerol, ethanol, and a mixture thereof. In addition, the vaccine may contain a small amount of an auxiliary substance (for example, a humidifying agent or an emulsifying agent), a pH buffering agent, and an adjuvant for enhancing the efficacy of the vaccine, if desired. Examples of adjuvants which can be efficacious include, but not limited to, the following: aluminium hydroxide, N-acetyl-muramyl-L-threonyl-D-isoglutamine (thr-MDP), N-acetyl-nor-muramyl-L-alanyl-D-isoglutamine (called CGP11637, nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (called CGP19835A, MTP-PE)), and RIBI. RIBI contains three ingredients extracted from bacteria, i.e., monophosphoryl lipid A, trehalose dimycolate and cell wall skeleton (HPL+TDM+CWS), in a 2% squalene/Tween (trade name) 80 emulsion. The efficacy of the adjuvant can be determined by measuring the amount of an antibody generated after administering a vaccine comprising GRA7 or AMA1.

The vaccine preparation of the present invention is typically administered by injection such as subcutaneous, intravenous or intramuscular injection. Different prescriptions suitable for other administration modes include a suppository and in some cases oral and nasal prescriptions.

If desired, one or more compounds having an adjuvant activity may be added. Adjuvants are non-specific stimulatory factors of the immune system. They enhance the immune response of a host to the vaccine. Specific examples of adjuvants known in the art include Freund's complete and incomplete adjuvants, vitamin E, non-ionic block polymer, muramyldipeptide, saponin, mineral oil, vegetable oil, and carbopol. Examples of adjuvants suitable particularly for application to the mucous membrane include *Escherichia coli* (*E. coli*) heat-labile toxin (LT) or cholera toxin (CT). Other suitable adjuvants include, for example, aluminum hydroxide, ammonium phosphate or aluminium oxide, oil emulsion (e.g., Bayol (trade name) or Marcol 52 (trade name)), saponin or vitamin E solubilisate. Thus, a preferred form of the vaccine of the present invention contains an adjuvant.

For example, in an injectable solution administered subcutaneously, intradermally, intramuscularly or intravenously, specific examples of a different pharmaceutically acceptable carrier or diluent capable of administered together with the vaccine of the present invention include a stabilizer, a carbohydrate (e.g., sorbitol, mannitol, starch, cane sugar, glucose, or dextran), a protein such as albumin or casein, a protein-containing material such as bovine serum or skim milk, and a buffer (e.g., phosphate buffer).

The amount to be administered, of the antigen typically ranges from 0.01 µg to 100,000 µg per administration and depends on the subject treated (e.g., mammal such as cattle, sheep, goats, deer, or dogs), the ability of the subject to synthesize antibody in the immune system thereof and the desired degree of protection and also depends on the administration route such as the oral, subcutaneous, nasal, intradermal, intramuscular or intravenous route of administration.

The vaccine preparation of the present invention can be given on a single administration schedule or preferably on a multiple administration schedule. For the multiple administration schedule, individual administration can be carried out 1 to 10 times in a beginning period of vaccination, followed by performing another administration at a time interval necessary for maintaining or boosting the immune response, for example, after 1 to 4 months as the second administration. Subsequently, administration can be carried out after several months, if necessary. An administration regimen is also at least partially determined by the individual's necessity and depends on the doctor's judgment.

In addition, the vaccine of the present invention may be prophylactically used for fresh *Neospora caninum* infection. Further, it may be used as a therapeutic vaccine for eliminating *Neospora caninum* by the administration thereof to a subject infected with *Neospora caninum* for the induction of a strong immune reaction to *Neospora caninum* in the living body.

The vaccine of the present invention is administered to subjects infected with *Neospora caninum* and thereby induces an immune response to a GRA7 or AMA1 protein to prevent *Neospora caninum* infection.

EXAMPLES

The present invention is described below in detail, based on Examples. However, the invention is not intended to be limited by these Examples.

Example 1

Preparation of *Neospora caninum*-Derived Soluble Protein

GRA7, AMA1 and SRS2 genes (GenBank ID U82229, AB265823 and U93870, respectively) were cloned from *Neospora caninum*. Based on each of the genes, a recombinant protein in which glutathione S-transferase (GST) was fused was expressed in *E. coli*. The resultant recombinant protein was purified using Glutathione Sepharose 4B (from Amersham Pharmacia Biotech Inc.). In addition, using Detoxi-Gel™ Endotoxin Removing Gel (from Pierce Inc.), endotoxin was removed from the purified recombinant protein.

Example 2

Preparation of Artificial Glycolipid

To 2.5 to 5 mg of mannotriose (Man3) having the structure: Manα1→6 (Manα1→3) Man was added 600 µl of distilled water, which was then stirred for dissolution to prepare an oligosaccharide solution. On the other hand, DPPE was dissolved to a concentration of 5 mg/ml in a chloroform/methanol (1:1 by volume ratio) mixed solution to prepare a DPPE solution. NaBH$_3$CN was dissolved to a concentration of 10 mg/ml in methanol to prepare a NaBH$_3$CN solution. To 600 µl of the oligosaccharide solution were added 9.4 ml of the DPPE solution and 1 ml of the NaBH$_3$CN solution, which was then stirred and mixed. The reaction mixture was incubated at 60° C. for 16 hours to form an artificial glycolipid. The reaction mixture was purified using a silica gel column and a C18 reverse-phase column to provide an artificial glycolipid, M3-DPPE.

Example 3

Preparation of *Neospora Caninum*-Derived Soluble Protein-Including Liposome

Cholesterol, dipalmitoylphosphatidylcholine (DPPC) and mannotriosedipalmitoylphosphatidylethanolamine (M3-

DPPE) prepared in Example 2 or cholesterol and dipalmitoylphosphatidylcholine (DPPC) were mixed at a molar ratio of 10:10:1 or 1:1, respectively and dissolved in 2 ml of chloroform to prepare a lipid film in a 10-ml pear-shaped flask. To the lipid film was subsequently added 3.75 mg/ml of the *Neospora caninum*-derived soluble protein obtained in Example 1 (content: 0.5 mg/ml) to prepare liposomes by vortexing in a water bath at 40° C. The particle sizes of these liposomes were then selected 5 times while applying a pressure ranging from 0.2 to 1 MPa to a 1-μm filter using an extruder as a particle-size selector. Subsequently, the liposome solution was recovered by a centrifugation method and suspended using PBS (−) three times. The suspension was centrifuged, followed by removing the supernatant to remove the antigen not included in the liposomes. The resultant liposomes were analyzed to measure the cholesterol amount and the *Neospora caninum*-derived soluble protein using commercially available kits, Cholesterol E Test Wako (from Wako Pure Chemical Industries Ltd., 439-17501) and Modified Lowry Protein Assay Reagent Kit (from Pierce, 23240).

Example 4

Verification of Vaccine Effect of *Neospora caninum*-Derived Soluble Protein-Including Liposome For abbreviations of the liposome inclusions used in Examples below, "M3-GST" indicates a liposome having an oligosaccharide (Man3) on the surface, in which GST protein prepared as in Example 1 is included; "M3-GRA-7" indicates a liposome having an oligosaccharide (Man3) on the surface, in which GRA7 protein prepared as in Example 1 is included; "M3-AMA1" indicates a liposome having an oligosaccharide (Man3) on the surface, in which AMA-1 protein prepared as in Example 1 is included; and "M3-SRS2" indicates a liposome having an oligosaccharide (Man3) on the surface, in which SRS2 protein prepared as in Example 1 is included. "PBS" indicates a phosphate buffer solution; "GRA7" indicates GRA7 protein prepared as in Example 1, not included in the liposome; and "AMA1" indicates AMA1 protein prepared as in Example 1, not included in the liposome.

Figure 2:
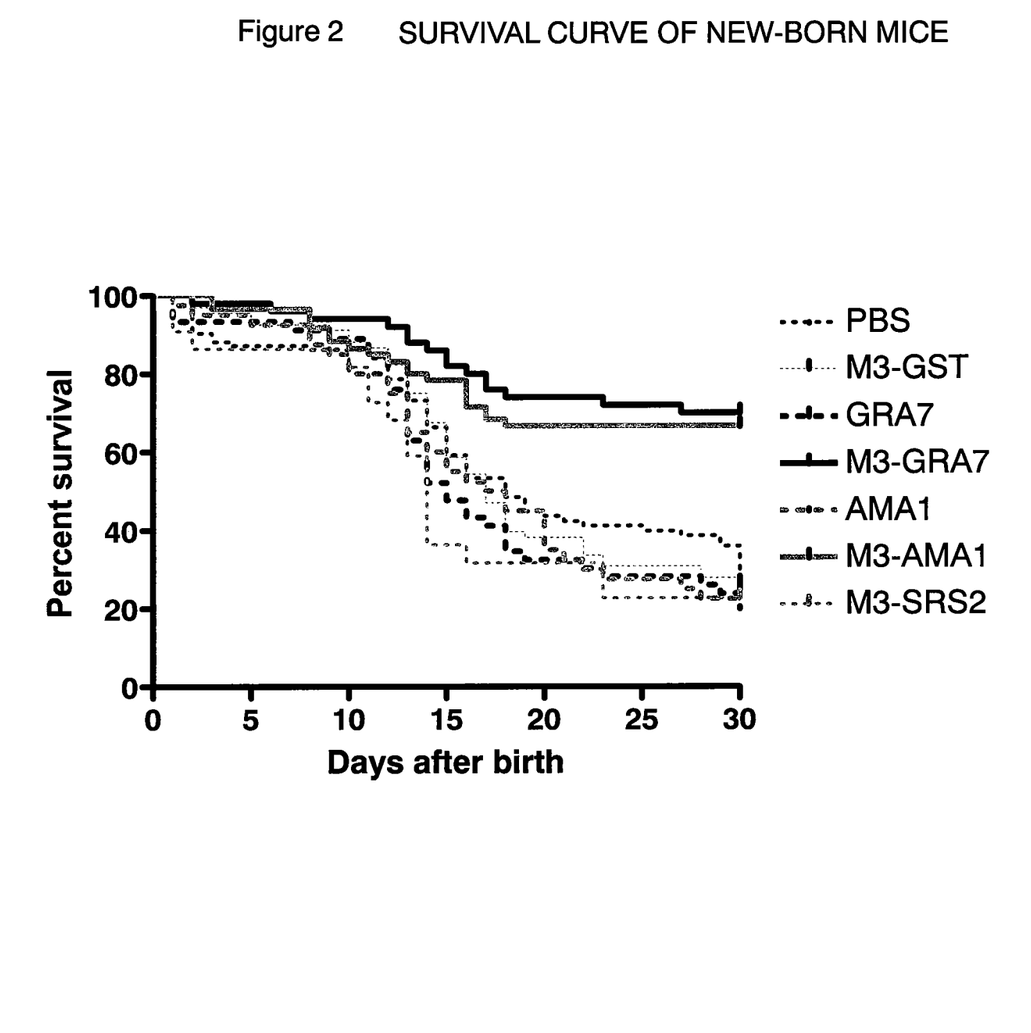
FIG. 2 is a graph showing the survival curve of newborn mice during a period of 30 days after birth.
Figure 3:
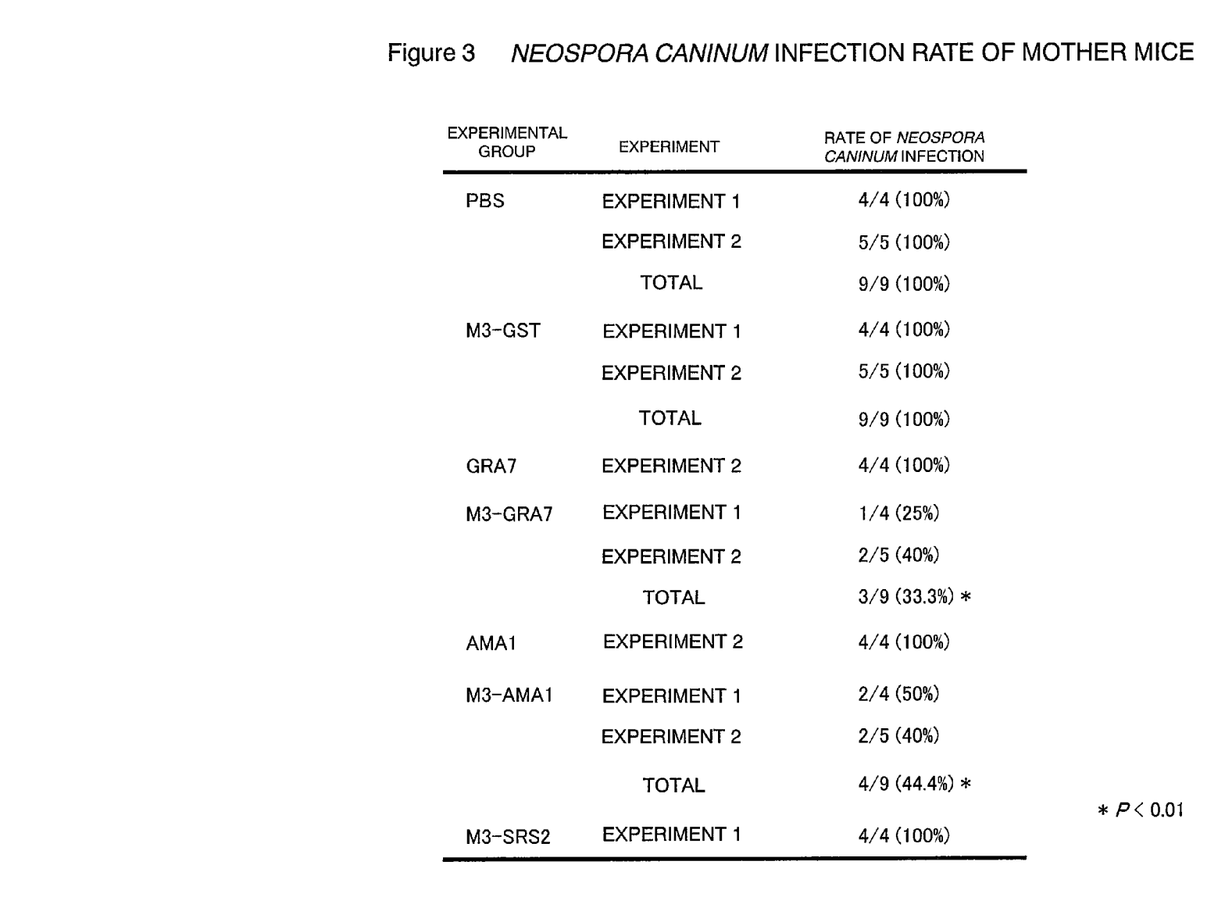
FIG. 3 is a drawing showing the *Neospora caninum* infection rate of mother mice.

*Neospora caninum*-derived soluble protein-including liposomes (40 nmol in terms of protein), each of various proteins (40 nmol in terms of protein) and PBS were each subcutaneously administered to BALB/c mice (6 weeks old, female) three times at one week intervals. One week after the third administration, these mice were crossed with male BALB/c mice (9 weeks old). At day 10 of gestation, 100,000 cells of *Neospora caninum* (tachyzoite) was intraperitoneally inoculated. The number of new-born mice was counted, and the survival rate (FIG. 1) and survival curve (FIG. 2) of the new-born mice during a postnatal period of 30 days were measured. In addition, at postnatal day 30, the brain was collected from the mother mice and analyzed for the presence of *Neospora caninum* infection using the PCR method (FIG. 3). The above experiment was performed three times; the first experiment is denoted by "trial 1", the second experiment, by "trial 2", and the third experiment, by "trial 3".

Figure 1:
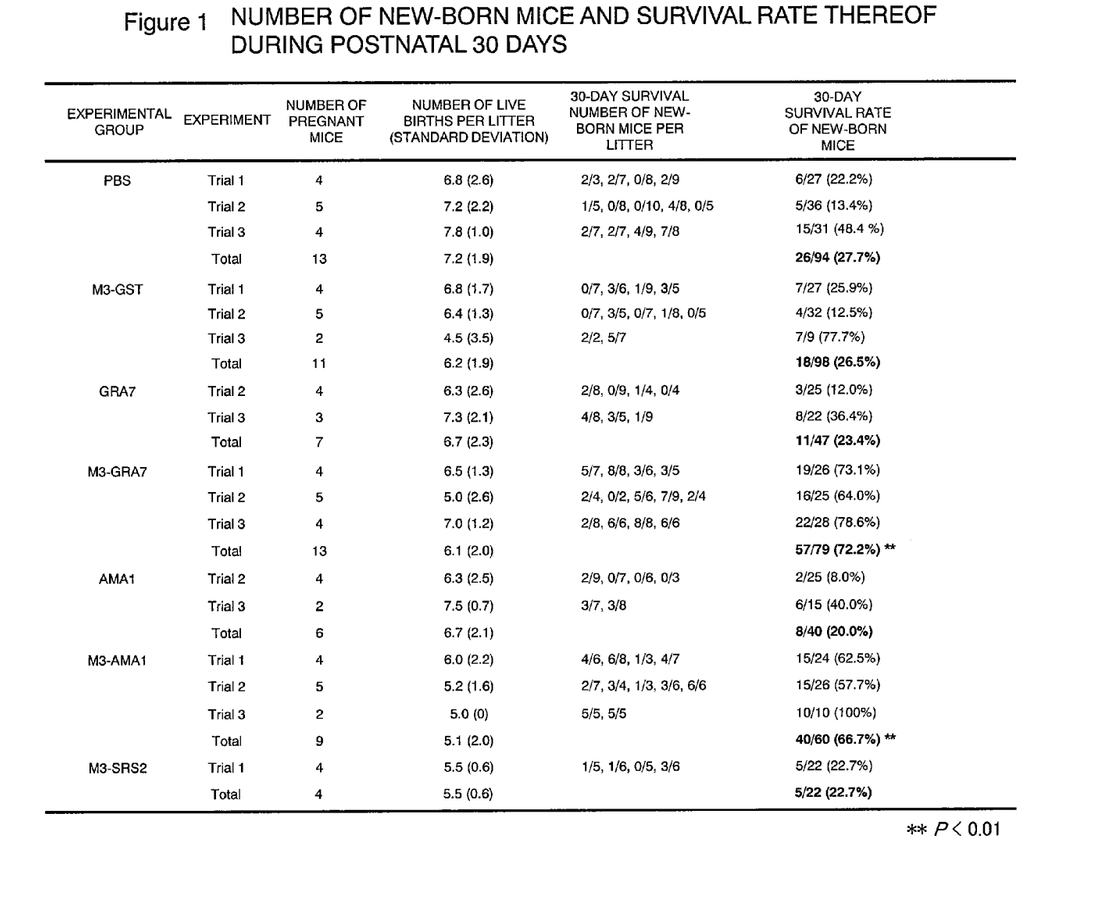
FIG. 1 is a drawing showing the number of newborn mice and the postnatal 30-day survival rate thereof.

When the number of live births per litter in each experimental group was compared with the number of live births per litter (8.3±1.5) in a group not immunized or infected, no significant difference was observed (FIG. 1, Student's t-test, determined at $p<0.01$). The results indicate that the administration of the liposomes or the proteins did not affect the number of live births in mice.

When the 30-day survival rate of new-born mice in each experimental group was compared with the result for the PBS administration group, increases in the survival rate of new-born mice were observed in the M3-GRA7 administration group and the M3-AMA1 administration group (FIG. 1, chi-test, determined at $p<0.01$). From the experimental results of trial 1, trial 2 and trial 3, the 30-day survival curve of new-born mice in each experimental group was prepared. As a result, the new-born mice tended to die at between postnatal day 12 and day 17 in the M3-GRA7 administration group and the M3-AMA1 administration group, while the new-born mice tended to die at between postnatal day 10 and day 22 in other administration groups (FIG. 2). These results indicate that the administration of GRA7 protein or AMA1 protein-including oligosaccharide liposomes can protect the mice from the vertical infection thereof with *Neospora caninum*.

When the rate of *Neospora caninum* infection in mother mice of each experimental group is compared with the result for the PBS administration group, decreases in the infection rate were observed in the M3-GRA7 administration group and the M3-AMA1 administration group (FIG. 3, chi-test, determined at $p<0.01$). In addition, it was demonstrated that the administration of M3-GRA7 most effectively suppressed the *Neospora caninum* infection.

The results obtained in FIGS. 1, 2 and 3 demonstrated that no vaccine effect was induced by combinations of a liposome and all of the *Neospora caninum*-derived antigens or heterologous antigens because no vaccine effect was observed in an M3-GST or M3-SRS2 administration group. This indicates that the combination of a liposome and the most suitable antigen (e.g., GRA7 or AMA1) is important for the induction of a vaccine effect.

Example 5

Production of *Neospora caninum*-Specific Antibody by Oligosaccharide Liposome Treatment in Mice

*Neospora caninum*-derived soluble protein-including liposomes (40 nmol in terms of protein), each of various proteins (40 nmol in terms of protein) and PBS were each subcutaneously administered to BALB/c mice (6 weeks old, female) three times at one week intervals. Blood was collected before the first administration and on day 7, day 14 and day 21 after the first administration, and plasma was obtained. Antigen-specific IgG, IgG1 and IgG2a antibodies were measured by an ELISA method using as antigens the same proteins (FIG. 4) or the *Neospora caninum* soluble antigens (FIG. 5, Student's t-test, determined at $p<0.01$) used in the respective experiment groups. In the PBS administration group of FIG. 4, the antibody production using GST as an antigen was measured.

Figure 4:
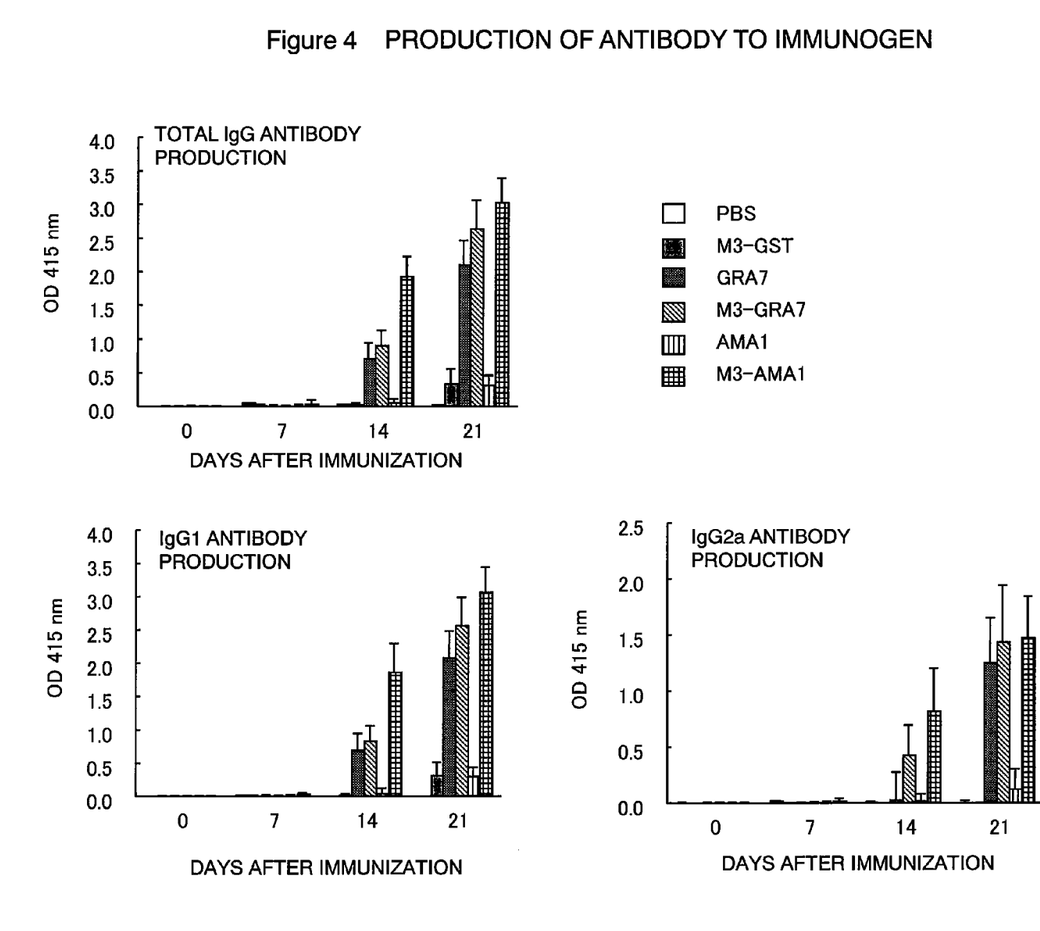
FIG. 4 is a set of graphs showing the levels of IgG, IgG1 and IgG2a antibodies specific for included antigens in the plasma of mice treated with the test substances.

In the GRA7 administration group, the production of GRA7-specific IgG, IgG1 and IgG2a antibodies were observed from 14 days after priming. In the M3-GRA7 administration group, the production of the GRA7-specific IgG, IgG1 and IgG2a antibodies tended to be slightly increased compared to that in the GRA7 administration group. In the AMA1 administration group, the production of AMA1-specific IgG, IgG1 and IgG2a antibodies was observed from 21 days after priming. In M3-AMA1 administration group, the production of AMA1-specific IgG, IgG1 and IgG2a antibodies was observed from 14 days after priming, and the antibody production was stimulated compared to that in the AMA1 administration group. These results showed that the *Neospora caninum* soluble proteins could be each included in liposomes for immunization to promote the production of an antibody specific for the included antigen.

Figure 5:
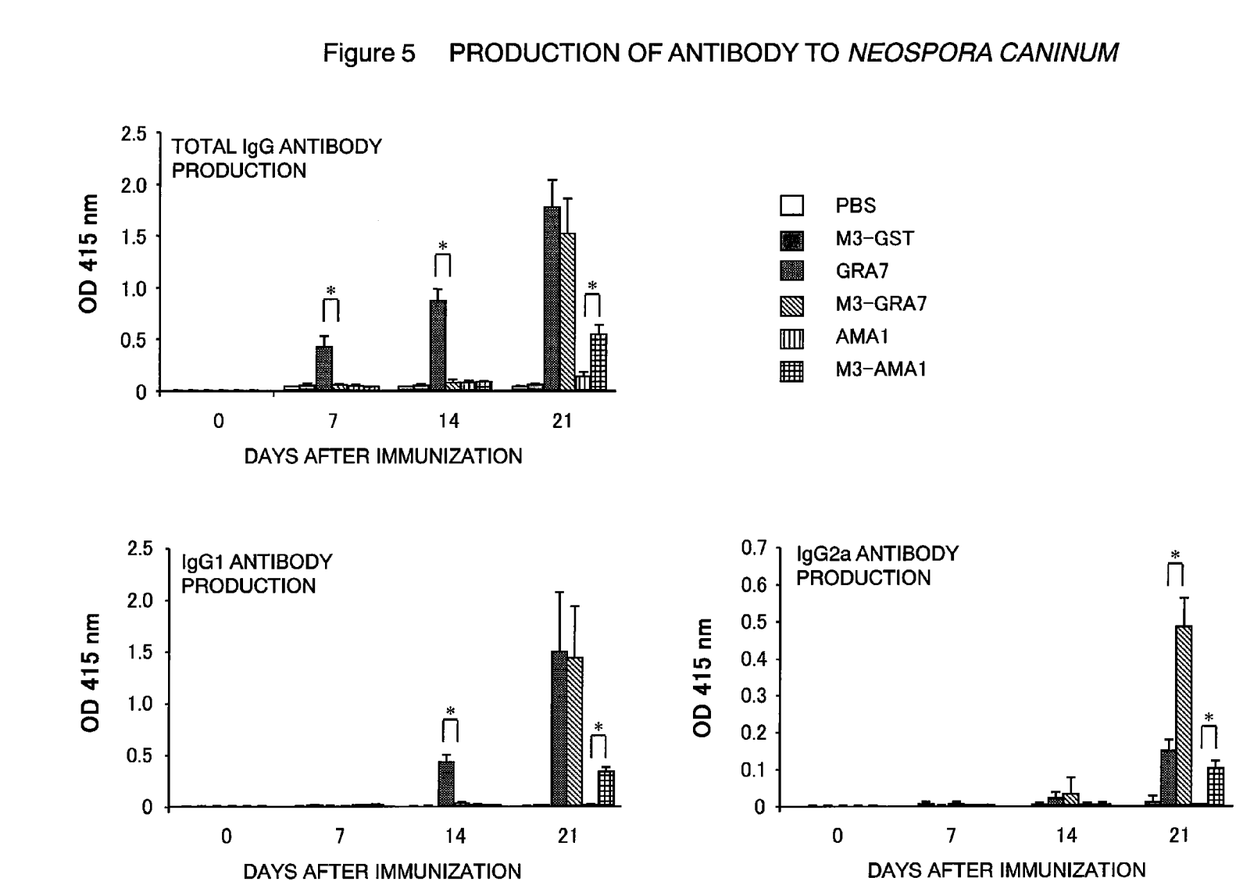
FIG. 5 is a set of graphs showing the levels of IgG, IgG1 and IgG2a antibodies specific for *Neospora caninum*-derived soluble antigens in the plasma of mice treated with the test substances.

The production of antibodies to *Neospora caninum* soluble antigens was then analyzed. In the GRA7 administration group, the production of *Neospora caninum* soluble antigen-specific IgG and IgG1 antibodies was observed 7 days and 14 days after priming. In the M3-GRA7 administration group, the production of *Neospora caninum* soluble antigen-specific IgG and IgG1 antibodies was observed 21 days after priming at the same level as that in the GRA7 administration group. An IgG2a antibody was significantly produced in the M3-GRA7 administration group compared to in the GRA administration group. In the AMA1 administration group, the significant production of *Neospora caninum* soluble antigen-specific antibodies was not observed. In the M3-AMA1 administration group, the production of *Neospora caninum* soluble antigen-specific IgG, IgG1 and IgG2a antibodies was observed 21 days after priming. These results showed that the *Neospora caninum* soluble proteins could be each included in liposomes for immunization to promote the production of an antibody specific for the same protein as the included antigen present in *Neospora caninum* and to induce humoral immunity (IgG1 antibody production was an index) and cellular immunity (IgG2a antibody production was an index) to the *Neospora*. Because no inclusion of the antigen in liposomes reduced the induction efficiency of IgG2a antibody, it was suggested that the inclusion thereof in liposomes could effectively promote the production of the IgG2a antibody and induce cellular immunity specific for the included antigen.

Example 6

Response of *Neospora caninum*-Specific Spleen Cell to Oligosaccharide Liposome Treatment in Mice

*Neospora caninum*-derived soluble protein-including liposomes (40 pmol in terms of protein), each of various proteins (40 pmol in terms of protein) and PBS were each subcutaneously administered to BALB/c mice (6 weeks old, female) three times at one week intervals. One week after the final administration, the spleen was removed and homogenized to prepare a spleen cell suspension ($5 \times 10^6$ cells/ml, RPMI1640 medium). A spleen cell suspension from each individual was cultured for 48 hours in a $CO_2$ incubator in the presence of a *Neospora caninum* soluble antigen (NLA, final concentration: 50 μg/ml), AMA1 (final concentration: 10 μg/ml) or GRA7 (final concentration: 10 μg/ml) or under unstimulated conditions (medium), followed by recovering the culture supernatant. Interferon gamma (IFN-γ, Th1 was used as a reaction index) and interleukin (IL)-4 (IL-4, Th2 was used as a reaction index) in the recovered culture supernatant were measured by an EIA method (FIG. 6, Student's t-test, determined at $p<0.01$).

Figure 6:
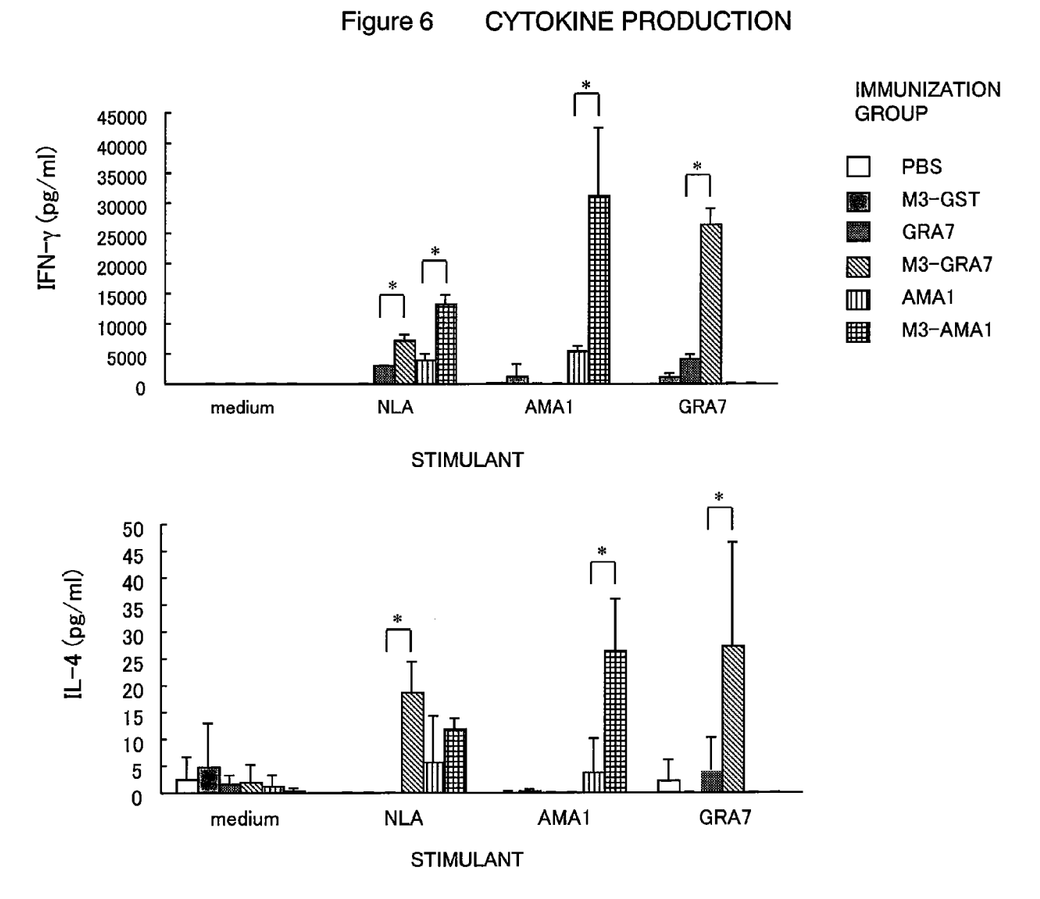
FIG. 6 is a pair of graphs showing the amount of antigen stimulation-specific IFN-γ and IL-4 production in mouse spleen cells treated with test substances.

As a result of measuring IFN-γ production in spleen cells, spleen cells in the M3-GRA7 administration group were found to produce IFN-γ in response to stimulation by NLA and GRA7. This production was at a higher level than that for the IFN-γ production of spleen cells in the GRA7 administration group. Spleen cells in the M3-AMA1 administration group produced IFN-γ in response to stimulation by NLA and AMA1. This production was at a higher level than that for the IFN-γ production of spleen cells in the AMA1 administration group. The IFN-γ production of spleen cells in the M3-GRA7 administration group and in the M3-AMA1 administration group was not observed under unstimulated conditions or conditions stimulated by the heterologous antigen.

As a result of measuring IL-4 production in spleen cells, spleen cells in the M3-GRA7 administration group were found to produce IL-4 in response to stimulation by NLA and GRA7. This production was at a higher level than that for the IL-4 production of spleen cells in the GRA7 administration group. Spleen cells in the M3-AMA1 administration group produced IL-4 at a higher level in response to stimulation by AMA1 than that for spleen cells in the AMA1 administration group. The IL-4 production of spleen cells in the M3-GRA7 administration group and in the M3-AMA1 administration group was at an extremely low level under unstimulated conditions or conditions stimulated by the heterologous antigen. However, the production amount of IL-4 measured in this experiment was 50 pg/ml or less, and thus the efficiency of inducing IL-4 production can be determined to be low.

Considering the results of the IL-4 production and the IFN-γ production under unstimulated conditions in spleen cells of each experimental group, spleen cells in the M3-GRA7 administration group and spleen cells in the M3-AMA1 administration group were shown to exhibit a Th1 response to stimulation by *Neospora caninum*.

These results demonstrated that oligosaccharide liposomes in which GRA7 or AMA1 as a *Neospora caninum* soluble protein is included can be subcutaneously administered to induce *Neospora caninum*-specific antibody production and a Th1 response for protection from the spread to the brain and vertical infection of the protozoon. Thus, it was determined that the oligosaccharide liposome in which the *Neospora caninum* soluble protein was included according to the present invention could be used as an effective vaccine for *Neospora caninum* infection. It was also determined that the vaccine preparation provided in the present invention has good safety in the perinatal period.

All publications, patents, and patent applications cited in this application are intended to be incorporated herein by reference in their entirety.

Industrial Applicability

According to the present invention, a vaccine preparation for *Neospora caninum* infection is provided which is safe and has a high prophylactic effect. The vaccine preparation according to the present invention can prevent the vertical infection of the fetuses with *Neospora caninum* as well as the infection of vaccinated individuals therewith, and is useful in the livestock industry and the like in which *Neospora caninum* infection is serious.

The invention claimed is:

1. A vaccine preparation for *Neospora caninum* infection, comprising a liposome preparation in which *Neospora caninum*-derived dense granule protein 7 is included in liposomes each having an oligosaccharide capable of binding to a carbohydrate recognition molecule on the surface of antigen-presenting cells on the surface of the liposome and a pharmaceutically acceptable carrier, wherein the dense granule protein 7 is:
(a) a protein comprising the amino acid sequence shown in SEQ ID NO: 1; or
(b) a protein comprising an amino acid sequence in which one or several amino acids are deleted, substituted, or added in the amino acid sequence shown in SEQ ID NO: 1 and capable of inducing an immune response to *Neospora caninum*.

2. The vaccine preparation according to claim 1, wherein the vaccine preparation is subcutaneously, intradermally, orally, or nasally administered.

3. The vaccine preparation according to claim 1, wherein the dense granule protein 7 is a protein comprising the amino acid sequence shown in SEQ ID NO: 1.

4. The vaccine preparation according to claim 1, wherein the carbohydrate recognition molecule on the surface of antigen-presenting cells is a mannose receptor.

5. The vaccine preparation according to claim 1, wherein the oligosaccharide consists of 2 to 11 sugar residues.

6. The vaccine preparation according to claim 1, wherein the oligosaccharide consists of 3 to 5 sugar residues.

7. The vaccine preparation according to claim 1, wherein the oligosaccharide comprises two or more mannose sugar residues.

8. The vaccine preparation according to claim 1, wherein the dense granule protein 7 is a protein comprising an amino acid sequence in which one or several amino acids are deleted, substituted, or added in the amino acid sequence shown in SEQ ID NO: 1 and capable of inducing an immune response to *Neospora caninum*.

* * * * *

UNITED STATES PATENT AND TRADEMARK OFFICE
CERTIFICATE OF CORRECTION

PATENT NO.       : 8,821,882 B2
APPLICATION NO.  : 13/119629
DATED            : September 2, 2014
INVENTOR(S)      : Yoshifumi Nishikawa et al.

Page 1 of 1

It is certified that error appears in the above-identified patent and that said Letters Patent is hereby corrected as shown below:

In the specification:

Column 5, line 23; please delete the word "MICS" and replace it with --MIC3--

Signed and Sealed this
Eighth Day of September, 2015

Michelle K. Lee
*Director of the United States Patent and Trademark Office*

SEQUENCE LISTING

<160> NUMBER OF SEQ ID NOS: 2

<210> SEQ ID NO 1
<211> LENGTH: 217
<212> TYPE: PRT
<213> ORGANISM: Neospora caninum

<400> SEQUENCE: 1

Met Ala Arg Gln Ala Thr Phe Ile Val Ala Leu Cys Val Cys Gly Leu

```
  1               5                   10                  15
Ala Ile Ala Gly Leu Pro Arg Leu Ala Ser Ala Gly Asp Leu Ala Thr
                20                  25                  30
Glu Gln His Glu Gly Asp Ile Gly Tyr Gly Val Arg Ala Tyr Ala Gly
                35                  40                  45
Val Ser Asn Tyr Asp Gly Asp Asp Ala Ala Gly Asn Pro Val Asp
        50                  55                  60
Ser Asp Val Thr Asp Asp Ala Ile Thr Asp Gly Glu Trp Pro Arg Val
65                  70                  75                  80
Val Ser Gly Gln Lys Pro His Thr Thr Gln Lys Gly Ser Leu Ile Lys
                85                  90                  95
Lys Leu Ala Val Pro Val Gly Ala Leu Thr Ser Tyr Leu Val Ala
                100                 105                 110
Asp Arg Val Leu Pro Glu Leu Thr Ser Ala Glu Glu Gly Thr Glu
                115                 120                 125
Ser Ile Pro Gly Lys Lys Arg Val Lys Thr Ala Val Gly Ile Ala Ala
        130                 135                 140
Leu Val Ala Ala Ala Phe Ala Gly Leu Gly Leu Ala Arg Thr Phe
145                 150                 155                 160
Arg His Phe Val Pro Lys Lys Ser Lys Thr Val Ala Ser Glu Asp Ser
                165                 170                 175
Ala Leu Gly Asn Ser Glu Glu Gln Tyr Val Glu Gly Thr Val Asn Gly
                180                 185                 190
Ser Ser Asp Pro Glu Gln Glu Arg Ala Gly Gly Pro Leu Ile Pro Glu
                195                 200                 205
Gly Asp Glu Gln Glu Val Asp Thr Glu
                210                 215
```

<210> SEQ ID NO 2
<211> LENGTH: 564
<212> TYPE: PRT
<213> ORGANISM: Neospora caninum

<400> SEQUENCE: 2

```
                  5                   10                  15
Met Gly Ser Trp Arg Arg Glu Arg Pro Ala Arg Pro Ser Asp Gln Gln
1                   5                   10                  15
Trp Ile Thr Glu Trp Arg Gln Ile Gly Ile Val Gly Val Ala Ile Leu
                20                  25                  30
Leu Val Leu Val Ala Glu Ser Ser Leu Leu Ala Thr Gly Ile Asn Pro
                35                  40                  45
Lys Thr Arg Ser Gly Gly Ser Gln Thr Leu Ser Ala Ser Thr Pro Gln
        50                  55                  60
Asn Pro Phe Gln Thr Pro Glu Leu Lys Ala Phe Leu Glu Arg Tyr Asn
65                  70                  75                  80
Val Thr Leu His His Gln Ser Gly Val Asn Val Asp Leu Gly Gln Asp
                85                  90                  95
Lys Glu Val Asp Gly Lys Leu Tyr Arg Glu Ala Ala Gly Leu Cys Pro
                100                 105                 110
Val Trp Gly Lys Tyr Ile Gln Leu His Gln Pro Asn Arg Pro Pro Tyr
                115                 120                 125
Lys Asn Asn Phe Leu Glu Asp Ile Pro Thr Glu Ala Glu Tyr Gln Lys
        130                 135                 140
Ser Gly Asn Pro Leu Pro Gly Gly Phe Asn Met Asn Phe Val Thr Pro
145                 150                 155                 160
```

```
Ala Gly Gln Arg Ile Ser Pro Tyr Pro Met Glu Leu Leu Glu Lys Ser
            165                 170                 175

Ser Lys Ile Lys Ala Ser Thr Glu Leu Gly Lys Cys Ala Glu Phe Ala
            180                 185                 190

Tyr Lys Thr Thr Ala Met Asp Lys Ser Asn Gln Ala Thr Gln Tyr Arg
            195                 200                 205

Tyr Pro Phe Val Tyr Asp Ser Lys Arg Arg Leu Cys Tyr Ile Leu Ser
            210                 215                 220

Val Ser Met Gln Arg Met Glu Gly Ser Lys Tyr Cys Ser Thr Asn Asp
225                 230                 235                 240

Asp Pro Val Asn Leu Thr Trp Tyr Cys Phe Glu Pro Gln Lys Ser Pro
            245                 250                 255

Thr Ala Asn His Asn Leu Ile Phe Gly Ser Ala Tyr Val Gly Lys Asp
            260                 265                 270

Pro Asp Ala Phe Leu Thr Lys Cys Pro Asn Gln Ala Leu Lys Gly Tyr
            275                 280                 285

Arg Phe Gly His Trp Thr Asn Gly Arg Cys His Asp Tyr Thr Glu Leu
            290                 295                 300

Ala Asp Ser Trp Ile Glu Ala Val Asp Ser Lys Ala Gln Cys Trp Val
305                 310                 315                 320

Lys Thr Phe Thr Asn Asp Glu Val Ala Ser Asp Gln Pro Arg Thr Tyr
            325                 330                 335

Pro Leu Thr Ser Gln His Ser Trp Asn Asp Trp Pro Val His Glu
            340                 345                 350

Lys Asp Gln Pro His Ser Gly Gly Asp Gly Arg Asn Tyr Gly Phe Phe
            355                 360                 365

Tyr Phe Asp Ser Asn Gly Lys Gly Lys Cys Ala Leu Ser His Lys Ala
            370                 375                 380

Pro Asp Cys Leu Val Ser Asp Ser Lys Ala Val Ser Tyr Thr Ala Leu
385                 390                 395                 400

Gly Ser Leu Ser Glu Glu Thr Pro Asp Ile Ile Pro Ser Asn Pro
            405                 410                 415

Ser Val Asn Pro Ser Thr Pro Asp Glu Ala Leu Gln Cys Arg Ser Ser
            420                 425                 430

Glu Phe Pro Glu Thr Phe Gly Ser Cys Asp Val Gln Ala Cys Lys Arg
            435                 440                 445

Gln Lys Thr Ser Cys Val Gly Gly Gln Ile Gln Ser Thr Ser Val Asp
            450                 455                 460

Cys Thr Ala Glu Glu Gln Asn Asp Cys Gly Ser Asn Thr Ala Leu Ile
465                 470                 475                 480

Ala Gly Met Ala Ile Gly Gly Val Leu Ile Met Gly Leu Leu Ala Gly
            485                 490                 495

Ser Gly Tyr Tyr Tyr Ser Lys Arg Leu Asn Thr Asn Gln Gly Val Pro
            500                 505                 510

Ala Val Asp His Asp His Glu Phe Gln Thr Gln Arg Asn Ala Gln Lys
            515                 520                 525

Lys Arg Pro Ser Asp Leu Met Gln Glu Ala Glu Pro Ser Phe Trp Asp
            530                 535                 540

Glu Ala Glu Glu Asn Ile Asp Gln Ser Gly Glu Thr Gln Val Leu Val
545                 550                 555                 560

Glu Gly Asp Tyr
```